United States Patent
Heerlein et al.

(10) Patent No.: US 9,717,918 B2
(45) Date of Patent: Aug. 1, 2017

(54) HEADPIECES AND IMPLANTABLE COCHLEAR STIMULATION SYSTEMS INCLUDING THE SAME

(71) Applicant: Advanced Bionics AG, Staefa (CH)

(72) Inventors: Markus Michael Heerlein, Valencia, CA (US); Scott A. Crawford, Castaic, CA (US); Dave Nyberg, Frazier Park, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/023,372

(22) PCT Filed: Oct. 31, 2013

(86) PCT No.: PCT/US2013/067818
§ 371 (c)(1),
(2) Date: Mar. 19, 2016

(87) PCT Pub. No.: WO2015/065442
PCT Pub. Date: May 7, 2015

(65) Prior Publication Data
US 2016/0213936 A1  Jul. 28, 2016

(51) Int. Cl.
*A61N 1/372* (2006.01)
*A61N 1/375* (2006.01)
*A61N 1/36* (2006.01)
*H04R 25/00* (2006.01)

(52) U.S. Cl.
CPC ..... *A61N 1/37229* (2013.01); *A61N 1/36032* (2013.01); *A61N 1/3758* (2013.01); *H04R 25/554* (2013.01); *H04R 2225/51* (2013.01)

(58) Field of Classification Search
None
See application file for complete search history.

(56) References Cited

U.S. PATENT DOCUMENTS

| | | | |
|---|---|---|---|
| 4,026,276 A | 5/1977 | Chubbuck | |
| 4,352,960 A | 10/1982 | Dormer et al. | |
| 5,948,006 A | 9/1999 | Mann | |
| 7,260,435 B2 | 8/2007 | Ibrahim | |
| 7,800,078 B2 | 9/2010 | Colvin, Jr. et al. | |
| 8,027,735 B1 | 9/2011 | Tziviskos et al. | |
| 9,132,270 B2 * | 9/2015 | Vaishya | A61N 1/36032 |
| 2004/0044382 A1 | 3/2004 | Ibrahim | |
| 2007/0100385 A1 | 5/2007 | Rawat et al. | |
| 2007/0229279 A1 | 10/2007 | Yamazaki et al. | |
| 2008/0046034 A1 | 2/2008 | Ibrahim | |

(Continued)

FOREIGN PATENT DOCUMENTS

| | | |
|---|---|---|
| EP | 1944827 A2 | 1/2008 |
| WO | WO 03/076012 A1 | 9/2003 |

(Continued)

OTHER PUBLICATIONS

PCT International Search and Written Opinion dated Dec. 13, 2013 for PCT App. Ser. No. PCT/US2013/067818.

(Continued)

*Primary Examiner* — Brian T Gedeon
(74) *Attorney, Agent, or Firm* — Henricks, Slavin & Holmes LLP

(57) ABSTRACT

Cochlear implant headpieces with improved antenna positioning.

14 Claims, 7 Drawing Sheets

(56) References Cited

U.S. PATENT DOCUMENTS

| | | |
|---|---|---|
| 2008/0177353 A1 | 7/2008 | Hirota et al. |
| 2008/0315311 A1 | 12/2008 | Okamoto |
| 2009/0065588 A1 | 3/2009 | Aoki et al. |
| 2009/0222066 A1 | 9/2009 | Chen et al. |
| 2010/0114245 A1 | 5/2010 | Yamamoto et al. |
| 2011/0009925 A1 | 1/2011 | Leigh et al. |
| 2012/0002830 A1 | 1/2012 | Solum |
| 2012/0089202 A1 | 4/2012 | Staller |

FOREIGN PATENT DOCUMENTS

| | | |
|---|---|---|
| WO | WO 2012/047967 A1 | 4/2012 |
| WO | WO 2012/099756 A1 | 7/2012 |

OTHER PUBLICATIONS

Hassler et al., *Polymers for Neural Implants*, Journal of Polymer Science: Part B: Polymer Physics (2011) pp. 18-33.
Rogers Corporation, R/flex JADE® A Series data sheet (2009).

* cited by examiner

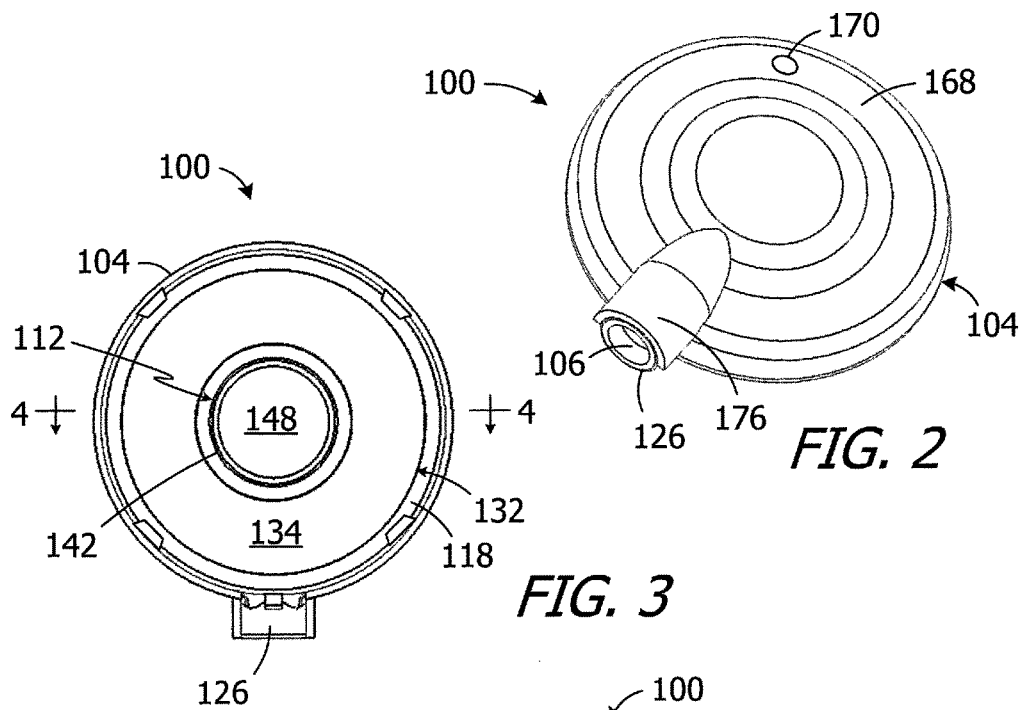
FIG. 2
FIG. 3
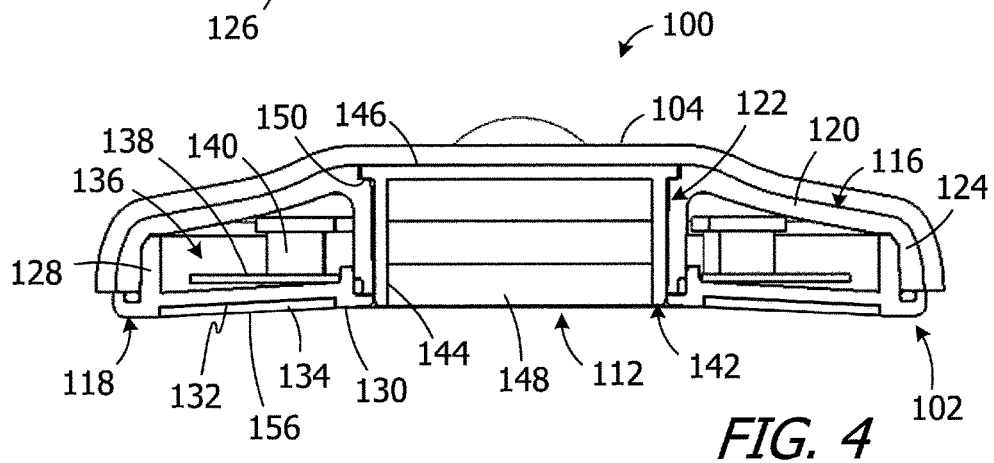
FIG. 4
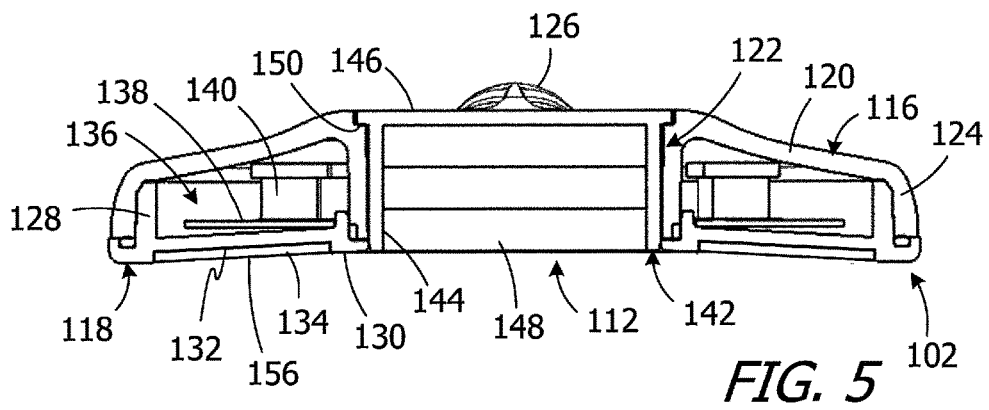
FIG. 5

HEADPIECES AND IMPLANTABLE COCHLEAR STIMULATION SYSTEMS INCLUDING THE SAME

CROSS-REFERENCE TO RELATED APPLICATIONS

This application is the U.S. National Stage of PCT App. Ser. No. PCT/US2013/067818, filed Oct. 31, 2013.

BACKGROUND

1. Field

The present disclosure relates generally to headpieces in implantable cochlear stimulation (or "ICS") systems.

2. Description of the Related Art

ICS systems are used to help the profoundly deaf perceive a sensation of sound by directly exciting the auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. A representative ICS system is disclosed in U.S. Pat. No. 5,824,022, which is entitled "Cochlear Stimulation System Employing Behind-The-Ear Sound Processor With Remote Control" and incorporated herein by reference in its entirety.

As alluded to above, some ICS systems include an implantable device, a sound processor unit, and a microphone that is in communication with the sound processor unit. The implantable device communicates with the sound processor unit and, to that end, some ICS systems include a headpiece that is in communication with both the sound processor unit and the implantable device. Such headpieces consist of a hollow housing with various components carried within the internal space. Communication between the headpiece and the implantable device is accomplished by way of an antenna carried on the printed circuit board within the headpiece housing and an antenna in the implantable device. In one type of ICS system, the sound processor unit is worn behind the ear (a "BTE unit"), while other types of ICS systems have a body worn sound processor unit (or "body worn unit"). The body worn unit, which is larger and heavier than a BTE unit, is typically worn on the user's belt or carried in the user's pocket. Examples of commercially available ICS sound processors include, but are not limited to, the Advanced Bionics Harmony™ BTE sound processor and the Neptune™ body worn sound processor.

The present inventors have determined that one issue associated with ICS systems is communication between the headpiece antenna and the implantable device antenna. In particular, the present inventors have determined that it would be desirable to provide a headpiece that is configured so as to decrease the distance between the headpiece antenna and the skin and, therefore the distance between the headpiece antenna and the implantable device antenna.

SUMMARY

A cochlear implant headpiece in accordance with one embodiment of a present invention comprises a housing including a bottom wall and an internal volume, a magnet mounted to the housing, a main circuit board located within the internal volume, and a headpiece antenna, configured to communicate with the cochlear implant antenna, that is not located on the main circuit board and is either mounted on or embedded within the bottom wall. The present inventions also include cochlear stimulation systems with a cochlear implant and such a headpiece.

A cochlear implant headpiece in accordance with one embodiment of a present invention comprises a housing including an internal volume and a bottom-most surface that abuts the top surface of the skin during use, a magnet mounted to the housing, a main circuit board located within the internal volume and a headpiece antenna, configured to communicate with the cochlear implant antenna, that is not located on the main circuit board and is carried by the housing such that the antenna is about 0.6 mm or less above the bottom-most surface.

There are a number of advantages associated with such headpieces and systems. For example, as compared to conventional headpieces, the present headpieces reduce the distance between the headpiece antenna and the cochlear implant antenna, for a given skin thickness, which results in more efficient power transmission. The present headpieces may also be used with patients having a wider range of skin thicknesses.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 2 is a perspective view of a headpiece in accordance with one embodiment of a present invention.

FIG. 3 is a bottom view of the headpiece illustrated in FIG. 2.

FIG. 4 is a section view taken along line 4-4 in FIG. 3.

FIG. 5 is a section view taken along line 4-4 in FIG. 3 with the headpiece cap removed.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions. It should also be noted that the description below uses the word "bottom" to describe structures that abut, face and/or are closer to the user's skin, and uses the word "top" to describe structures that face away from and/or are further from the user's skin. A "bottom portion" is, for example, closer to the user's skin than a "top portion."

The present inventions have application in a wide variety of systems that provide sound (i.e., either sound or a perception of sound) to the hearing impaired as well as others who require such systems on a situational basis. One example of such a system is an ICS system where an external sound processor communicates with a cochlear implant and, accordingly, the present inventions are discussed in the context of ICS systems. The present inventions are not, however, limited to ICS systems and may be used in combination with other systems for the hearing impaired that currently exist, or are yet to be developed.

Figure 1:
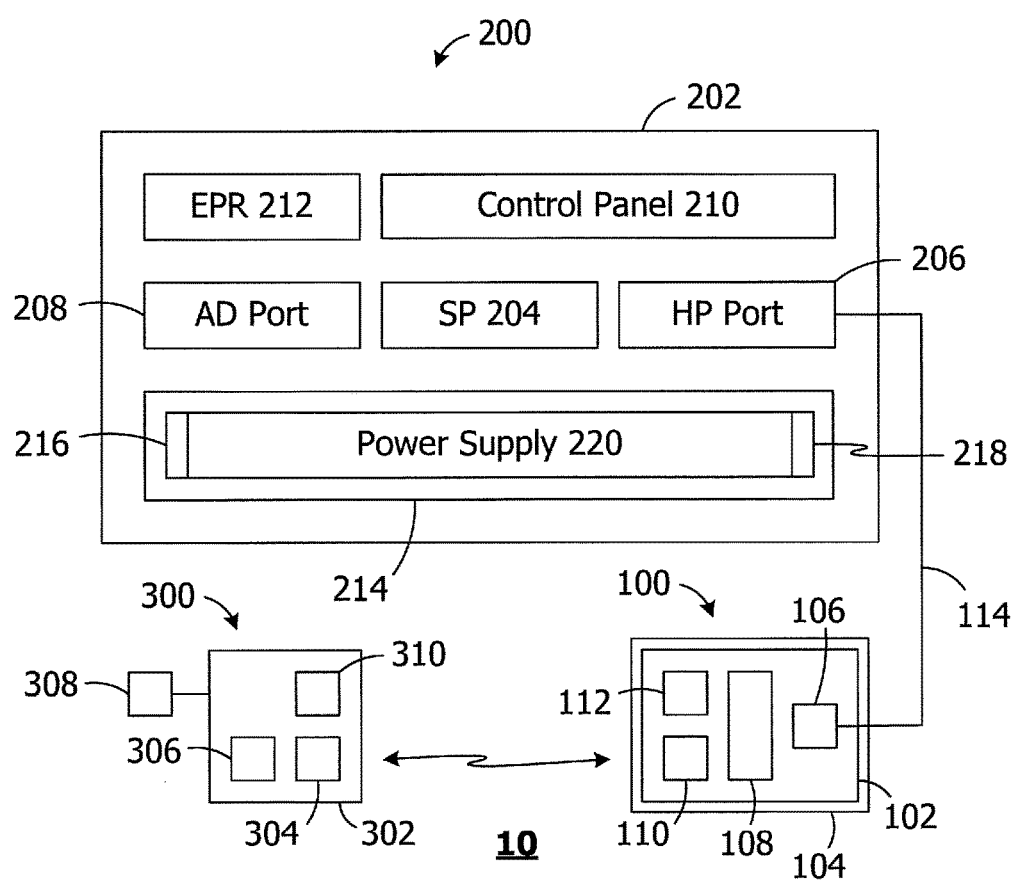
FIG. 1 is a functional block diagram of an ICS system in accordance with one embodiment of a present invention.

One example of an ICS system is generally represented by reference numeral 10 in FIG. 1. The system 10 includes a headpiece 100, a sound processor 200 and a cochlear implant 300.

The exemplary headpiece 100 includes a housing 102 and a removable cap 104, as well as various components, e.g., a RF connector 106, a microphone 108, an antenna 110 and a positioning magnet assembly 112, that are carried by the housing. The removable cap 104 may be omitted in some embodiments. Additional details concerning the headpiece 100, as well as headpieces 100a-100e, are described below with reference to FIGS. 2-19. For example, the headpiece 100 may be configured such that the antenna 110 is closer to the skin and, therefore, closer to the cochlear implant antenna than is the case with conventional headpieces.

The exemplary sound processor 200 includes a housing 202 in which and/or on which various components are supported. Such components may include, but are not limited to, sound processor circuitry 204, a headpiece port 206, an auxiliary device port 208 for an auxiliary device such as a mobile phone or a music player, a control panel 210 (including, e.g., a volume knob and program switch), a Euro Plug receptacle 212 (for a Euro Plug such as that associated with the Phonak MLxi FM receiver), and a power supply receptacle 214 with electrical contacts 216 and 218 for a removable battery or other removable power supply 220 (e.g., rechargeable and disposable batteries or other electrochemical cells). A power button (not shown) may also be carried on the housing 202. The headpiece port 206 and auxiliary device port 208 may be connected to the sound processor circuitry 204 by way of, for example, a signal splitter/combiner (not shown) such as that found in the Platinum Sound Processor body worn unit from Advanced Bionics.

The headpiece 100 in the exemplary ICS system 10 may be connected to the headpiece port 206 by a cable 114. In at least some implementations, the cable 114 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques.

The exemplary cochlear implant 300 includes a housing 302, an antenna 304, an internal processor 306, a cochlear lead 308 with an electrode array, and a positioning magnet (or magnetic material) 310. The antenna 110 and antenna 304 are respectively configured to communicate with one another by way of electromagnetic induction, radio frequencies, or any other wireless communication technology. The positioning magnet assembly 112 and positioning magnet (or magnetic material) 310 maintain the position of the headpiece antenna 110 over the cochlear implant antenna 304.

During use, the microphone 108 picks up sound from the environment and converts the sound into electrical impulses, and the sound processor 200 filters and manipulates the electrical impulses and sends the processed electrical signals through the cable 114 to the antenna 110. Electrical impulses received from an auxiliary device are processed in essentially the same way. The antenna 304 receives signals from the antenna 110 and sends the signals to the cochlear implant internal processor 306, which modifies the signals and passes them through the cochlear lead 308 to the electrode array. The electrode array may be wound through the cochlea and provides direct electrical stimulation to the auditory nerves inside the cochlea. This provides the user with sensory input that is a representation of external sound waves which were sensed by the microphone 108.

The exemplary sound processor 200 may be carried by the user in a variety of ways. By way of example, but not limitation, the sound processor 200 may be carried in the user's pocket, secured to a belt with a belt clip that is either part of housing 106 or a separate carrier, or placed in a harness that is configured to be worn by a small child. Sound processors that are integrated into headpieces are discussed below with reference to FIGS. 18 and 19.

Turning to FIGS. 2-5, and as noted above, the exemplary headpiece 100 includes a housing 102 and a removable cap 104 that may be secured to the housing. The housing 102 has a top portion 116 and bottom portion 118. The exemplary housing top portion 116 has a top wall 120, an aperture 122 for the magnet assembly 112, a housing microphone aperture (not shown), a side wall 124, and a connector tube 126 in which the connector 106 is located. The exemplary bottom portion 118 has a side wall 128 and a bottom wall 130 that extends slightly beyond the side wall. The bottom wall 130 is concave and includes an indentation (or recess) 132 for an antenna printed circuit board (PCB) 134, which is discussed in detail below with reference to FIG. 6, that is secured to the bottom wall. The indentation extends upwardly from the concave bottom-most surface of the bottom wall 130. Adhesive bonding, or any other suitable bonding technique may be employed. So arranged, the antenna 110 is under the bottom wall 130.

The configurations of the housing top portion 116 and bottom portion 118 are such that the inner surface of the top portion side wall 124 abuts the outer surface of the bottom portion side wall 128 when the housing 102 is in the assembled state. The housing 102 bottom portion 118 may be secured to the top portion 116 by joining the side walls 124 and 128 together with, for example, techniques such as ultrasonic welding. The exemplary housing 102 has an internal volume 136, defined by the top and bottom portions 116 and 118, in which the microphone 108 and a main PCB 138 are positioned. In the illustrated implementation, all of electronic components 140 (with the exception of the connector 106, microphone 108, and antenna 110) are carried on the main PCB 138. Components 140 include capacitors, resistors and inductors. The connector 106 and microphone 108 may be connected to the main PCB 138 by, for example, connector wires and microphone wires (not shown) that are soldered to the main PCB.

It should be noted here that the shape of the bottom wall 130 is selected so as to match the shape of the portion of the cochlear implant housing in which cochlear implant antenna is located. For example, in those instances where the portion of the cochlear implant housing in which the antenna is located has a convex surface that faces the skin, the shape of the bottom wall 130 will be concave. Such an arrangement facilitates headpiece retention as well as an even distribution of force/pressure on the skin. Similarly, in those instances where the portion of the cochlear implant housing in which the antenna is located has a flat surface that faces the skin, the headpiece antenna will also be flat (note FIG. 17).

The exemplary magnet assembly 112 includes a magnet housing 142, with a tubular member 144 and an end wall 146 that projects radially outward of the tubular member, and a plurality of magnets 148 located within the tubular member. The bottom surfaces of the tubular member 144 and bottom magnet 148 are aligned with one another. The magnets 148 may be secured to the tubular member 144 with a press-fit, adhesive, or any other suitable instrumentality. Although there are three magnets 148 in the assembly 112, this number may be increased or decreased to suit particular applications as is discussed below with reference to FIGS. 15 and 16. The edge of the end wall 146 rests within an indentation 150 in the housing top portion 116 that extends around the top end of the aperture 122, thereby limiting the downward movement of the magnet assembly 112. Upward movement is limited by the removable cap 104. As such, the magnet assembly 112 is held in place when the cap 104 is secured to the housing 102 (FIG. 4) and may be removed from the aperture 122 when the cap 104 is removed (FIG. 5). The housing 102 and magnet assembly 112 are also respectively configured such that the bottom surfaces of the housing bottom wall 130, the antenna PCB 134, the bottom magnet 148, and the tubular member 144 are aligned with one another in the manner shown to form the concave bottom surface of the headpiece 100. In some instances, a thin biocompatible coating may be applied to the bottom surface of the bottom magnet 148.

Figure 6:
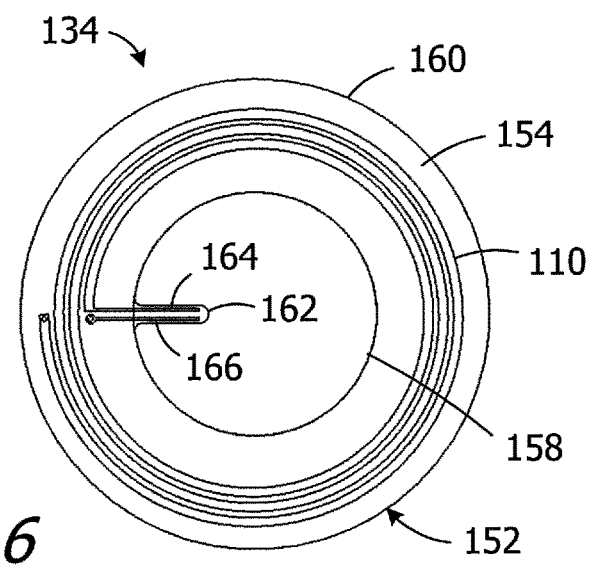
FIG. 6 is a top view of an antenna printed circuit board in accordance with one embodiment of a present invention.

Turning to FIG. 6, the antenna PCB 134 includes a thin substrate 152 and the antenna 110. In the illustrated implementation, the antenna 110 is a coil that is printed or otherwise formed on the top surface 154 of the substrate 152 along with additional insulation layers as needed. The top surface of antenna 110 may be coated with a layer of liquid crystal polymer or other electrically insulating material. The substrate also includes a bottom surface 156 (FIGS. 4 and 5) that faces the user's skin, thereby providing a thin barrier between the antenna and the skin, and inner and outer edges 158 and 160. A connection tab 162 extends inwardly from the inner edge 158. Leads 164 and 166 are connected to the free ends of the coil antenna 110 to the connection tab 162. Lead 166 is connected by way of a via and a conductor (not shown). During the assembly process, the antenna 110 is connected to the main PCB 138 by bending the connection tab 162, inserting the tab 162 into the internal volume 136 by way of an aperture (not shown) in the housing bottom portion 118, and then soldering the leads 164 and 166 to the main PCB 138.

The antenna PCB 134 also has a shape that corresponds to that of the bottom of the housing 102, as can be seen in FIGS. 4 and 5. In the illustrated embodiment, the antenna PCB 134 has a frusto-conical shape and may be shaped by thermoforming or other suitable processes.

Suitable materials for the substrate 152 include, but are not limited to, liquid crystal polymer, sealed polyimide, and other biocompatible materials. The thickness of the substrate may range from about 0.1 mm to about 0.5 mm, and is about 0.15 mm in the illustrated example. As used herein in the context of an antenna PCB, the term "about" means +/−0.05 mm. It should be noted here that the antennas in the present inventions are not limited to antenna PCBs. Other antenna assemblies, such as those which include an antenna that is produced apart from the substrate and then mounted thereon, may be employed. In any case, the depth of the indentation 132 may be equal to the thickness of the antenna PCB 134, or other antenna assembly, so that the bottom surface of the headpiece 100, as defined by the bottom surfaces of the housing 102, magnet assembly 112 and the antenna PCB 134, is a smooth concave surface.

There are a number of advantages associated with configuring a headpiece such that the distance between the antenna and the skin is reduced to the thickness of a thin substrate. For example, the distance between the headpiece antenna and the cochlear implant antenna is reduced, which results in more efficient power transmission. Additionally, the decrease in headpiece antenna to skin surface spacing allows the headpiece to be used with broader range of skin thicknesses. In particular, the headpiece and implant antennas (and associated circuitry) may be respectively configured (or "tuned") to be most efficient at a particular skin thickness (e.g. 5.0 mm, which is 1.0 mm greater than the typical skin thickness) and to be operable within a range of thicknesses that are above the particular thickness. Decreasing the distance between the headpiece antenna and the skin surface increases the range of acceptable skin thicknesses above the particular skin thickness, thereby allowing the headpiece to be used with a broader range of patients.

For example, a cochlear implant antenna is frequently located 4.0 mm below the outer surface of the skin, while some conventional headpieces position the headpiece antenna 2.0 mm above the outer surface of skin when the headpiece is on the head, which results in a 6.0 mm distance between the headpiece antenna and the cochlear implant antenna. The present headpiece antenna 110, on the other hand, is only 0.15 mm from the skin surface when the headpiece is positioned on the head and, accordingly, is 4.15 mm from the cochlear implant antenna. This represents an a 30% reduction in the antenna to antenna spacing, and a 90% reduction in the spacing between the headpiece antenna and the skin surface, as compared to the conventional headpiece location described above. These numbers will change slightly in those instances where there is hair between the headpiece and the skin surface. Integrating the antenna into the bottom wall 130 of the housing 102, without increasing the thickness thereof, also allows the overall height of the headpiece to be reduced.

Figure 7:
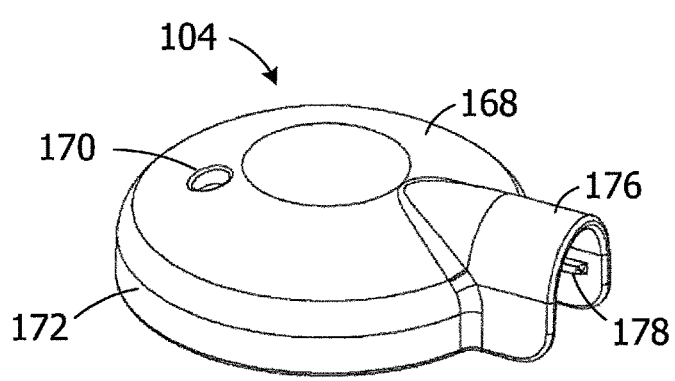
FIG. 7 is a perspective view of a headpiece cap in accordance with one embodiment of a present invention.
Figure 8:
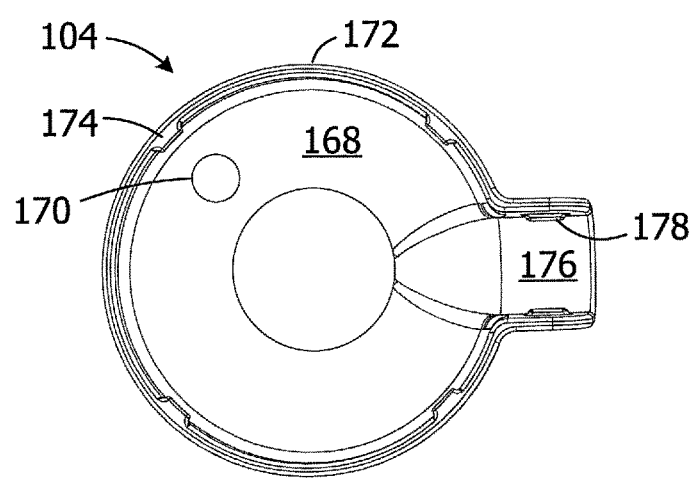
FIG. 8 is a bottom view of the headpiece cap illustrated in FIG. 7.

The removable cap 104 in the illustrated embodiment may be connected to and then removed from the housing 102, i.e., the cap may be removably connected to the housing. Referring to FIGS. 7 and 8, the exemplary cap 104 includes a top wall 168 with a sound port 170 that aligns with the microphone aperture (not shown) in the housing 102, a side wall 172 with a plurality of latches 174, and a connector hood 176 with a pair of latches 178. The respective configurations of the housing 102 and cap 104 allow the cap to be snap fit onto the housing and removed from the housing. In particular, the cap latches 174 will be aligned with housing latch indentations (not shown) when the housing 102 and cap 104 are oriented in the manner illustrated in FIGS. 2 and 3. The distance between the inner surfaces of the hood latches 166 is less than the diameter of the connector tube 126, and the distance between the hood 176 is greater than the diameter of the connector tube. The cap 104 is also somewhat flexible. Thus, as the cap 104 is pressed onto the housing 102, the cap side wall 172 and hood 176 will bow outwardly as the latches 174 and 178 slide along the housing side wall 124 and connector cover 126. When the cap 104 reaches the position illustrated in FIGS. 2 and 3, the resilience of the cap will force the latches 174 into the latch recess and the hood latches 178 against the surface of the connector cover 126, thereby latching the cap to the housing 102. The cap 104 may be removed by pulling the cap at the free end of the hood 176.

Figure 9:
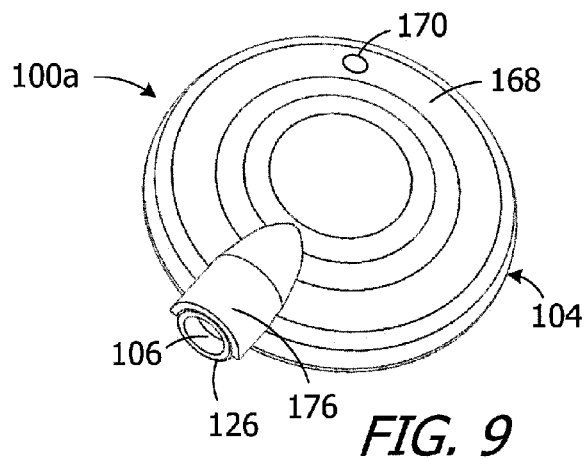
FIG. 9 is a perspective view of a headpiece in accordance with one embodiment of a present invention.
Figure 10:
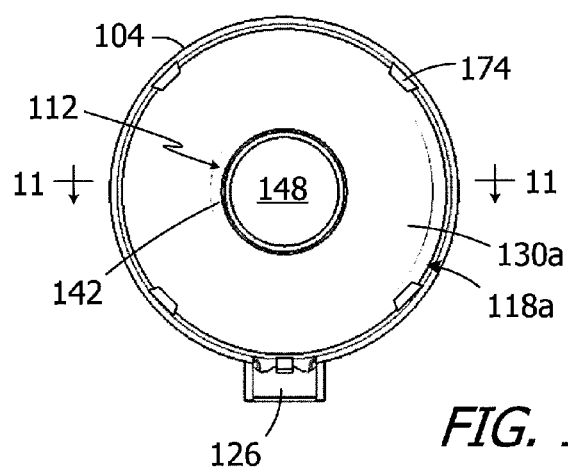
FIG. 10 is a bottom view of the headpiece illustrated in FIG. 9.
Figure 11:
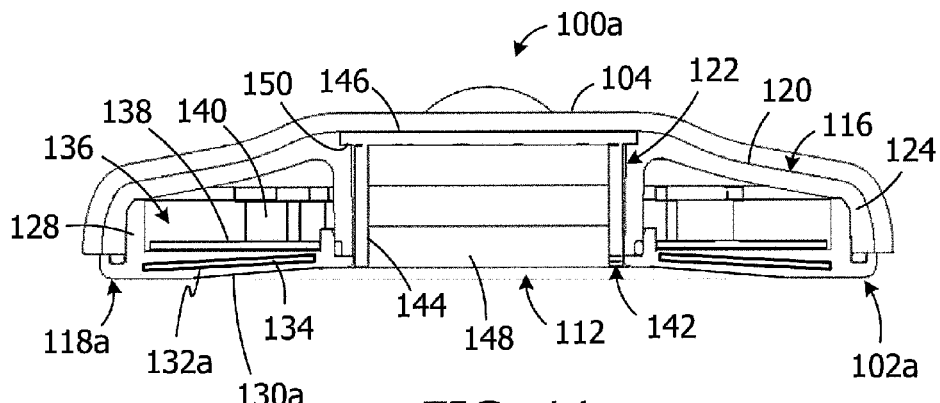
FIG. 11 is a section view taken along line 11-11 in FIG. 10.

Another exemplary headpiece is generally represented by reference numeral 100a in FIGS. 9-11. Headpiece 100a is substantially similar to headpiece 100 and similar elements are represented by similar reference numerals. Here, however, the antenna PCB 134 (which includes the substrate 152 and the antenna 110) is embedded within the bottom wall 130a of the bottom portion 118a of the housing 102a. In other words, a void 132a within the bottom wall 130a is occupied by the antenna PCB 134. The bottom portion 118a may, for example, be overmolded onto the antenna PCB 134 through an injection molding process. The concave bottom surface of the headpiece 100a is, therefore, defined by the bottom surfaces of the magnet assembly 112 and the bottom wall 130a.

The antenna 110 will be about 0.4 mm from the skin surface when the headpiece 100a is positioned on the head. Although embedding the antenna PCB 134 results in a slight increase in the distance between the headpiece antenna 110 and the implanted antenna as compared to headpiece 100, the distance is significantly smaller than that associated with conventional headpieces, as discussed above, while the embedding improves durability and facilitates the use of non-biocompatible materials.

Figure 12:
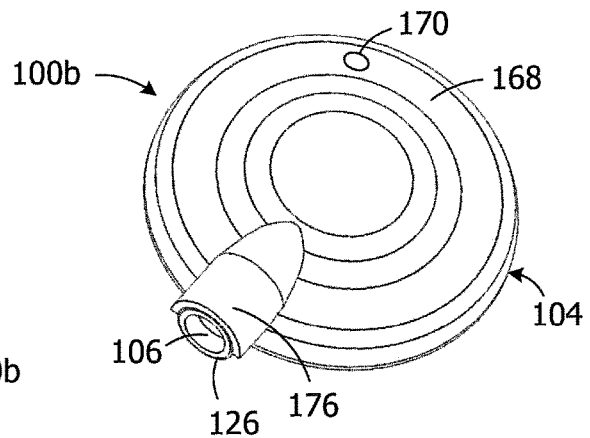
FIG. 12 is a perspective view of a headpiece in accordance with one embodiment of a present invention.
Figure 13:
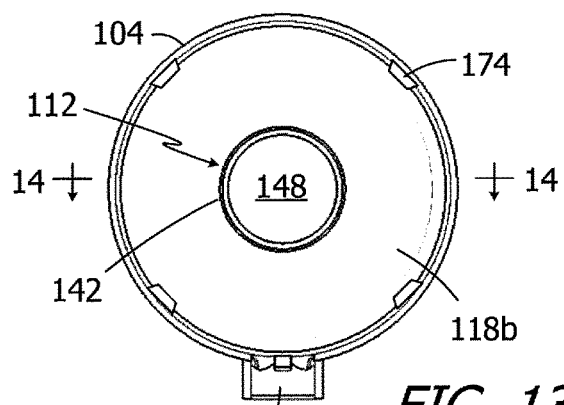
FIG. 13 is a bottom view of the headpiece illustrated in FIG. 12.
Figure 14:
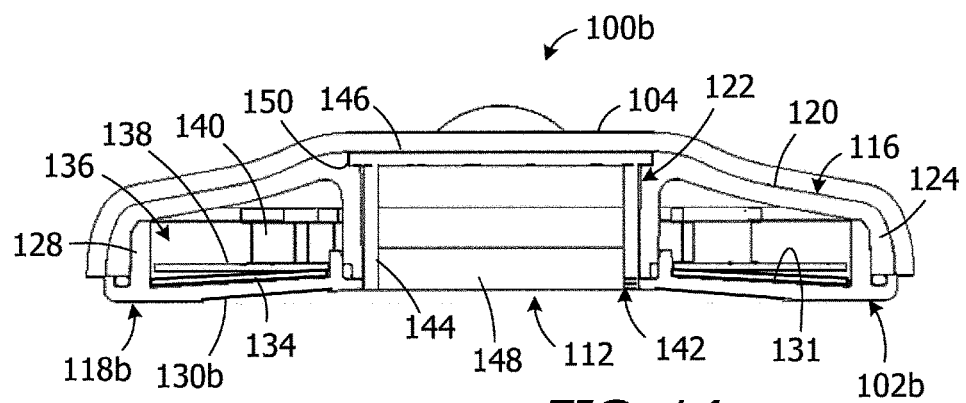
FIG. 14 is a section view taken along line 14-14 in FIG. 13.

Another exemplary headpiece is generally represented by reference numeral 100b in FIGS. 12-14. Headpiece 100b is substantially similar to headpiece 100 and similar elements are represented by similar reference numerals. Here, however, the antenna PCB 134 (which includes the substrate 152 and the antenna 110) is located within the internal volume 136 of the housing 102b under the main PCB 138. More specifically, the antenna PCB 134 is located on, and is bonded to, the top surface 131 of the bottom wall 130b. The concave bottom surface of the headpiece 100b is, therefore, defined by the bottom surfaces of the magnet assembly 112 and the bottom wall 130b. The bottom wall top surface 131 has a sloped, or frusto-conical, shape so that the antenna PCB 134 (and antenna 110) will be shaped the same manner also illustrated in FIGS. 5 and 11.

The antenna 110 will be about 0.6 mm from the skin surface when the headpiece 100b is positioned on the head. Although securing the antenna PCB 134 to the bottom wall top surface results in a slight increase in the distance between the headpiece antenna 110 and the implanted antenna as compared to headpiece 100, the distance is significantly smaller than that associated with conventional headpieces, as discussed above, while the location within the internal volume 136 improves durability, facilitates the use of non-biocompatible materials and simplifies manufacturing.

Figure 15:
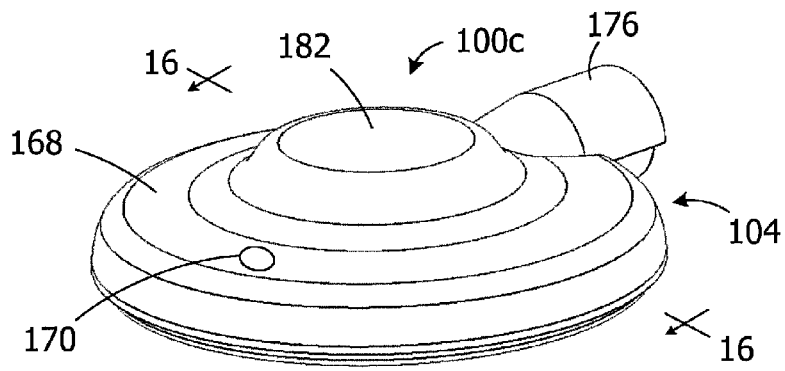
FIG. 15 is a perspective view of a headpiece in accordance with one embodiment of a present invention.
Figure 16:
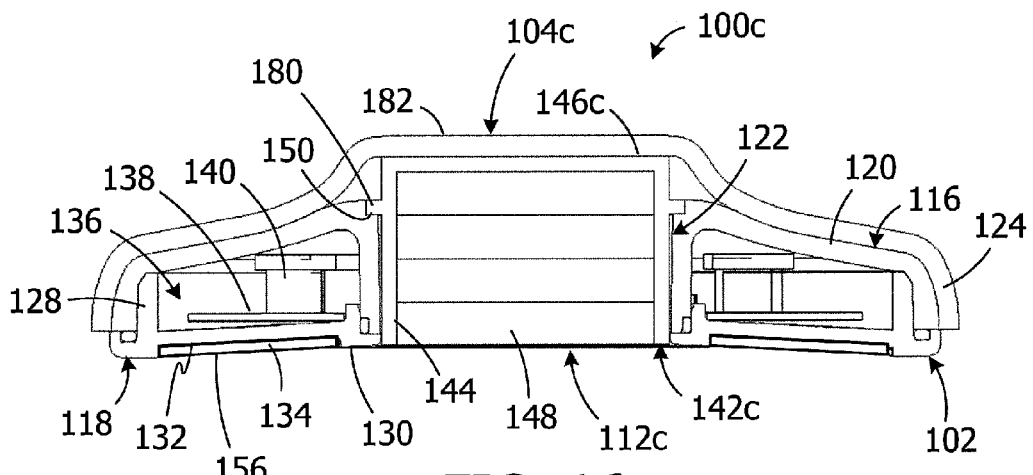
FIG. 16 is a section view taken along line 16-16 in FIG. 15.

As alluded to above, the number of magnets in the present headpieces may be increased or decreased as desired. For example, one of the magnets 148 in the magnet assembly 112 illustrated in FIGS. 4 and 5 may be removed and replaced with a non-magnetic spacer. The number of magnets may be increased in any of the embodiments described above by, for example, reconfiguring the cap and the magnet housing. The other aspects of the headpiece may remain unchanged. To that end, the exemplary headpiece generally represented by reference numeral 100c in FIGS. 15 and 16 is substantially similar to headpiece 100 and similar elements are represented by similar reference numerals. Here, however, there are four magnets 148 in the magnet assembly 112c and the magnet housing 142c is enlarged (as compared to magnet housing 142) to accommodate the additional magnet. The tubular member 144c is long enough for four magnets, which results in the end wall 146c being above the indentation 150 in the housing top portion 116. An annular tab 180, which is located on the outer surface of the tubular member 144c, rests within the indentation 150. The cap 104c has a raised portion 182 for the upper end of the magnet assembly 112c.

Figure 17:
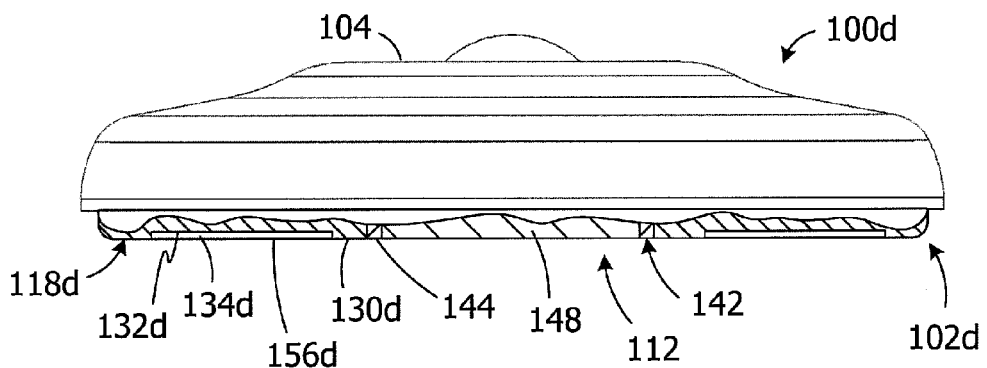
FIG. 17 is a front, cutaway view of a headpiece in accordance with one embodiment of a present invention.

Although the bottom surfaces of the headpieces 100-100c are concave, flat bottom surfaces may also be employed in each instance. For example, the exemplary headpiece 100d illustrated in FIG. 17 is substantially similar to headpiece 100 and similar elements are represented by similar reference numerals. Here, however, the housing 102d includes a bottom portion 118d that has a flat bottom wall 130d. The antenna assembly 134, as well as the antenna and substrate thereof, is also flat, as is the recess 132d.

Figure 18:
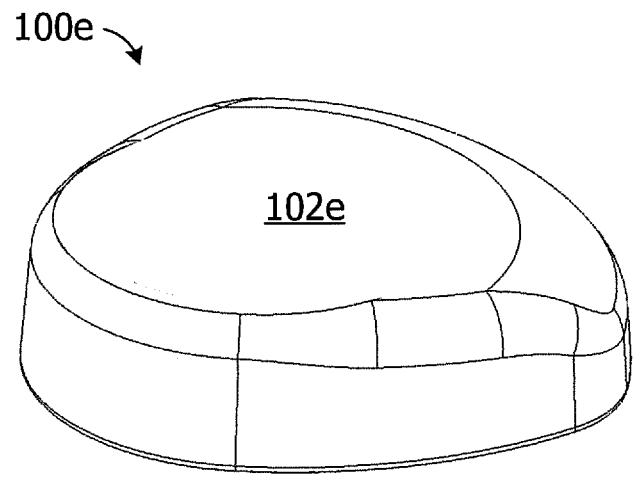
FIG. 18 is a perspective view of a headpiece in accordance with one embodiment of a present invention.
Figure 19:
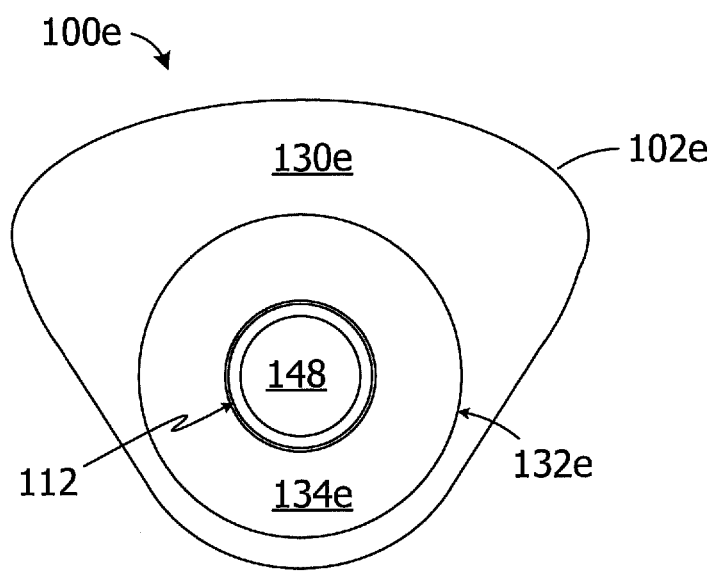
FIG. 19 is a bottom view of the headpiece illustrated in FIG. 18.

The present inventions are also applicable to headpieces that include all of the external components of a cochlear implant system. In addition to the aforementioned headpiece antenna coil and microphone, such headpieces also include sound processors and power supplies. By way of example, but not limitation, the headpiece 100e illustrated in FIGS. 18 and 19 is essentially identical to one of the headpieces illustrated and described in US Pat. Pub. No. 2010/0046778, which is incorporated herein by reference, but for the location of the headpiece antenna and associated modifications. The headpiece includes a housing 102e in which components (not shown) such as the sound processor, power supply and microphone are located. The flat bottom surface 130e of the housing 102e includes a recess 132e for a flat antenna assembly 134e. The housing 102e is also configured to accommodate a magnet assembly 112 or similar magnet arrangement. The antenna assembly may also be repositioned in manners described above with reference to FIGS. 11 and 14. The bottom surface 130e may also be reconfigured so as to include a concave region for a concave antenna assembly. Other examples of headpieces that have all of the external components of a cochlear implant system, and may be modified to embody the present inventions, include the other headpieces illustrated and described in US Pat. Pub. No. 2010/0046778 as well as the headpiece illustrated and described in US Pat. Pub. No. 2010/0046779, which is also incorporated herein by reference.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. The present inventions also include systems including headpieces in accordance with description above and claims below in combination with a sound processor and/or a cochlear implant. It is intended that the scope of the present inventions extend to all such modifications and/or additions and that the scope of the present inventions is limited solely by the claims set forth below.

We claim:

1. A cochlear implant headpiece for use with a cochlear implant having an antenna, comprising:
   a housing including a bottom wall defining a bottom surface and an internal volume;
   a magnet mounted to the housing;
   a main circuit board located within the internal volume; and
   a headpiece antenna, configured to communicate with the cochlear implant antenna, that is not located on the main circuit board and is mounted on, and is associated with the bottom surface of, the bottom wall.

2. A cochlear implant headpiece as claimed in claim 1, wherein
   the bottom surface of the bottom wall includes an indentation; and
   the headpiece antenna is located within the indentation.

3. A cochlear implant headpiece as claimed in claim 1, further comprising:
   a substrate on which the headpiece antenna is located.

4. A cochlear implant headpiece as claimed in claim 3, wherein
   the headpiece defines a bottom surface; and
   the housing bottom wall and the substrate define respective portions of the bottom surface of the headpiece.

5. A cochlear implant headpiece as claimed in claim 1, wherein
   wherein the housing defines a flat bottom.

6. A cochlear implant headpiece as claimed in claim 1, wherein
   wherein the housing defines a concave bottom.

7. A cochlear implant headpiece as claimed in claim 1, further comprising:
   a cap carried by the housing.

8. A cochlear implant headpiece as claimed in claim 1, further comprising:
   a sound processor within the housing.

9. A cochlear implant headpiece for use with a cochlear implant having an antenna that is located under skin having a top surface, comprising:
   a housing including an internal volume and a bottom-most surface that defines at least a portion of the bottom-most surface of the headpiece and abuts the top surface of the skin during use;
   a magnet mounted to the housing;
   a main circuit board located within the internal volume; and
   a headpiece antenna, configured to communicate with the cochlear implant antenna, that is not located on the main circuit board and is carried by the housing such that the antenna is about 0.6 mm or less above the bottom-most surface of the headpiece.

10. A cochlear implant headpiece as claimed in claim 9, wherein
    the headpiece antenna is about 0.15 mm above the bottom-most surface of the headpiece.

11. A cochlear implant headpiece as claimed in claim 10, further comprising:
    a substrate that is about 0.15 mm thick on which the headpiece antenna is located.

12. A cochlear implant headpiece as claimed in claim 9, wherein
    the bottom-most surface of the headpiece is concave.

13. A cochlear implant headpiece as claimed in claim 9, wherein
    the bottom-most surface of the headpiece is flat.

14. A cochlear implant system, comprising:
    a headpiece as claimed in claim 1; and
    a cochlear implant including a cochlear implant antenna.

* * * * *